United States Patent [19]

Indig et al.

[11] Patent Number: 5,043,053
[45] Date of Patent: Aug. 27, 1991

[54] REFERENCE ELECTRODE PROBE FOR USE IN AQUEOUS ENVIRONMENTS OF HIGH TEMPERATURE AND HIGH RADIATION

[75] Inventors: Maurice E. Indig, Fremont, Calif.; Laura L. H. King, Raleigh, N.C.

[73] Assignee: General Electric Company, San Jose, Calif.

[21] Appl. No.: 345,741

[22] Filed: May 1, 1989

[51] Int. Cl.$^5$ .......................................... G01N 27/30
[52] U.S. Cl. .................................. 204/421; 204/435
[58] Field of Search .............. 204/421, 422, 423, 435, 204/424

[56] References Cited

U.S. PATENT DOCUMENTS

| | | | |
|---|---|---|---|
| 3,784,459 | 1/1974 | Jackson | 204/423 |
| 4,096,048 | 6/1978 | Matsumoto et al. | 204/424 |
| 4,264,424 | 4/1981 | Niedrach | 204/421 |
| 4,575,410 | 3/1986 | Neti | 204/422 |

Primary Examiner—G. L. Kaplan
Attorney, Agent, or Firm—Robert R. Schroeder

[57] ABSTRACT

The reference electrode probe of the present invention utilizes a metal/metal oxide/$ZrO_2$ electrode sensor. Metal/metal oxide couples suitable include copper/copper oxide, tin/tin oxide, bismuth/bismuth oxide, and iron/iron oxide. The zirconia tube has a closed end and an open end. The closed end contains the metal/metal oxide powder and is retained therein by mineral insulation packing. A first annular metal sleeve is formed of metal exhibiting a coefficient of thermal expansion compatible with the zirconia tube and has a distal open end in sealing engagement with the open end of said zirconia tube. The first annular metal sleeve also has a proximal open end. An insulated first electrical conductor having a distal end in electrical connection with the metal/metal oxide powder extends through the mineral insulation packing and into the first annular sleeve. The first conductor also has a proximal end that terminates near the proximal end of the first annular sleeve. Advantageously, an annular ceramic tube is nested within said first annular metal sleeve and provides the insulation for the first electrical conductor. A signal transfer assembly is sealingly associated with the proximal end of the first annular sleeve. A second electrical conductor passes through the signal transfer assembly to its electrical connection with the first electrical conductor. The major advantages of the present invention over previous devices are its ability to withstand powerful radiation fields in high temperature, high pressure water; and construction features which avoid any leakage of the radioactive environment, which the sensor contacts, to the ambient.

16 Claims, 2 Drawing Sheets

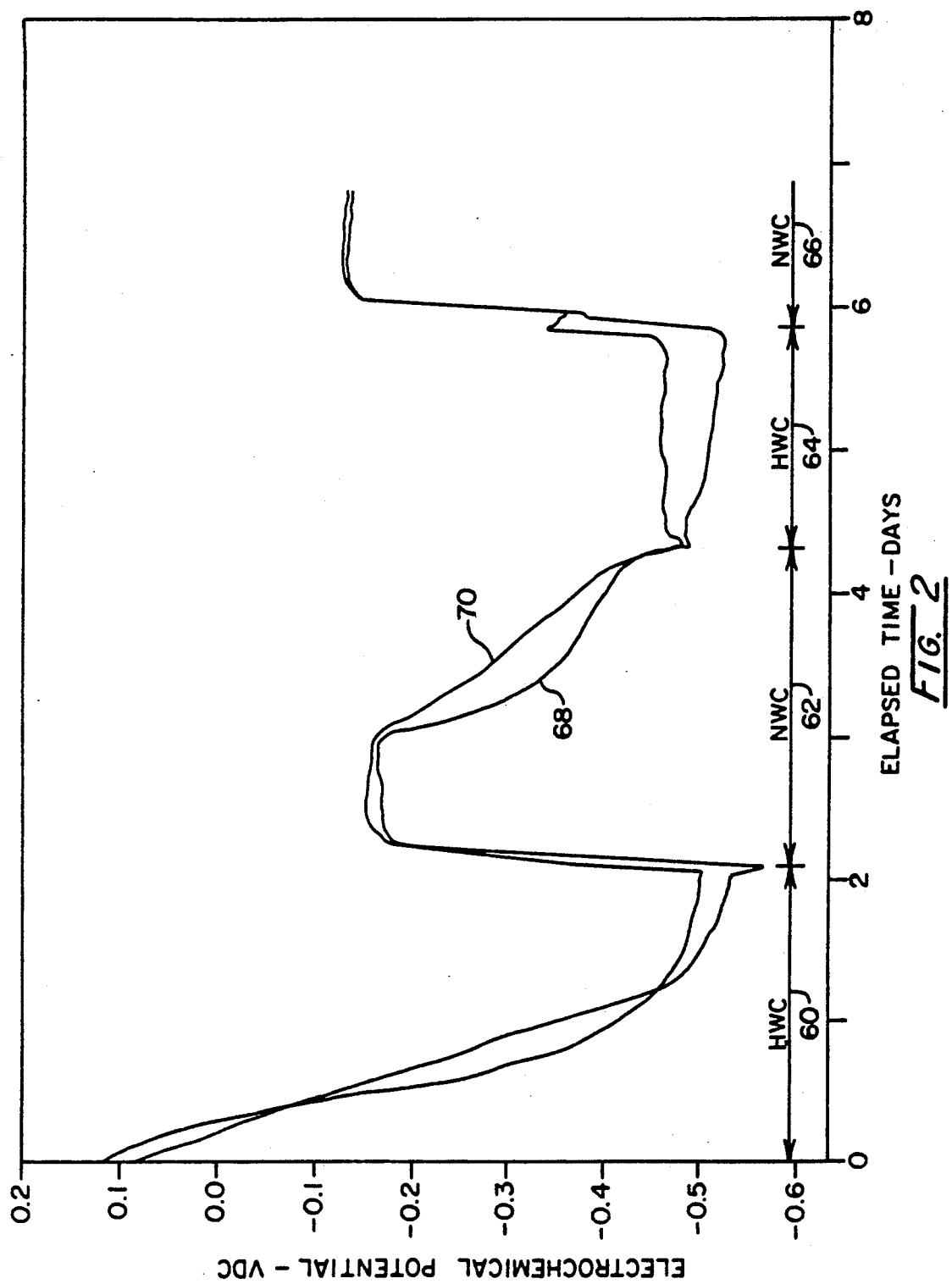

REFERENCE ELECTRODE PROBE FOR USE IN AQUEOUS ENVIRONMENTS OF HIGH TEMPERATURE AND HIGH RADIATION

BACKGROUND OF THE INVENTION

The nuclear power industry long has been engaged in a multitude of studies and investigations seeking improvement in the stamina and reliability of the materials and components forming a reactor based power system. One such investigation has been concerned with intergranular stress corrosion cracking (IGSCC) which heretofore principally has been manifested in the water recirculation piping systems external to the radiation intense reactor core regions of nuclear facilities. Typically, the piping architecture of these external systems is formed of a stainless steel material. Generally, these studies have determined that three factors must occur in coincidence to create IGSCC promotional conditions. These factors are: (a) a sensitization of the metal (stainless steel) for example, such as caused by a chromium depletion at grain boundaries which may be caused by heat treatment in the course of normal processing of the material or by welding and the like procedures; (b) the presence of tensile stress in the material; and (c) the oxygenated normal water chemistry (NWC) environment typically present in a boiling water reactor (BWR). This latter environment is occasioned by any of a variety of oxidizing species contributed by impurities in reactor coolant water. By removing any one of these three factors, the IGSCC phenomenon is essentially obviated. Such removal particularly has been accomplished with respect to the latter, oxygenated environment factor, through employment of an electrochemical potential monitoring approach combined with an associated hydrogen water chemistry (HWC) technique providing for a controlled addition or injection of hydrogen into the aqueous coolant environment.

Electrochemical potential monitoring is carried out employing paired electrochemical half-cell probes or electrodes which are mounted within the recirculation piping or in an external vessel which has its water source from the reactor water in the recirculation piping the electrodes are accessed to the external environment through gland type mountings or the like. Where, as in the instant application, the electrode system of interest involves the potential from a metal corrosion electrode, then the reference electrode can conveniently be a metal-insoluble salt-electrode if the metal salt couple is chemically stable and if appropriate thermodynamic data is available. Accordingly, one of the thus-mounted probes which is configured as a reference electrode may be based, for example, on a silver/silver chloride half-cell reaction. Once the reference electrode half cell is defined, the cell is completed with the sensing cell portion based upon a metal such as platinum or stainless steel. Calibration of the reference electrode and/or the electrode pair is carried out by appropriate Nernst based electrochemical calculations, and by thermodynamic evaluation in combination with laboratory testing within a known environment.

Half cell electrodes developed for use in reactor recirculation piping traditionally have been configured with metal housings, high temperature ceramics, and polymeric seals such as Teflon. These structures have performed adequately in the more benign and essentially radiation-free environments of recirculation piping.

Over the recent past, investigators have sought to expand the electrochemical potential (ECP) monitoring procedures to the severe environment of the fluid in the vicinity of the reactor core itself for the purpose of studying or quantifying the effect of hydrogen-water chemistry adjustment in mitigating irradiation assisted stress corrosion cracking (IASCC) as well as IGSCC. Within the reactor core, the monitoring electrode can be mounted, for example, with otherwise unemployed or in tandem with the traveling instrumentation probe (TIP) of available local power range monitors (LPRM) and the like. The monitors are located in a severe, high temperature (typically 285° C.), high pressure and high radiation (typically $10^9$R (rads) per hour gamma, $10^{13}$R per hour neutron) environments. Probe structures of earlier designs are completely inadequate for this reactor core environment, both from a material standpoint and with respect to the critical need to prevent leakage of radioactive materials to the environment outside of the reactor vessel.

BROAD STATEMENT OF THE INVENTION

The present invention is address to an electrode for evaluating electrochemical potentials which has a robust structure particularly suiting in for employment within the rigorous environment of the reactor core of a nuclear power facility.

The reference electrode probe of the present invention utilizes a metal/metal oxide/$ZrO_2$ electrode sensor. Metal/metal oxide couples suitably include copper/copper oxide, tin/tin oxide, bismuth/bismuth oxide, and iron/iron oxide. The zirconia tube has a closed end and an open end. The close end contains the metal/metal oxide powder and is retained therein by mineral insulation packing. A first annular metal sleeve is formed of metal exhibiting a coefficient of thermal expansion compatible with the zirconia tube and has a distal open end in sealing engagement with the open end of said zirconia tube. The first annular metal sleeve also has a proximal open end. An insulated first electrical conductor having a distal end in electrical connection with the metal/metal oxide powder extends through the mineral insulation packing and into the first annular sleeve. The first conductor also has a proximal end that terminates near the proximal end of the first annular sleeve. Advantageously, an annular ceramic tube is nested within said first annular metal sleeve and provides the insulation for the first electrical conductor. A signal transfer assembly is sealingly associated with the proximal end of the first annular sleeve. A second electrical conductor passes through the signal transfer assembly to its electrical connection with the first electrical conductor.

Advantages of the present invention include the ability of the electrode probe to function at elevate temperature with no leakage. The zero leakage characteristic allows the advantageous application of the inventive reference electrode to other remote reactor applications, where radiation levels per se may not be a problem on materials, but where any leakage of reactor water out of the containment poses concern. Failure of the zirconia tube does not result in leakage due to the seal at the proximal end of the first annular metal sleeve. Another advantage is the optimization of the brazing system that allow joining of the zirconia tube to a kovar first annular metal sleeve. These and other advantages will be readily apparent to those skilled in the art based upon the disclosure contained herein.

BRIEF DESCRIPTION OF THE DRAWING

FIG. 2 is a graph showing a laboratory evaluation of two different platinum sensing electrode probes as measured against the inventive reference electrode probe.

Figure 1:
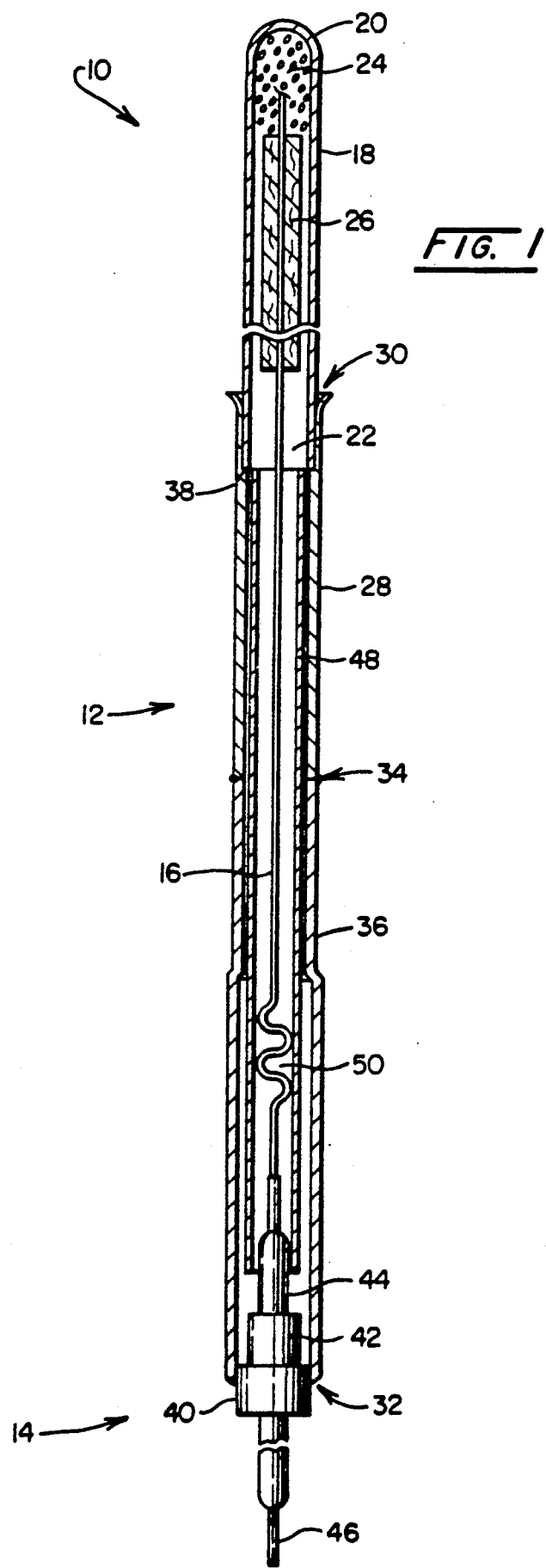
FIG. 1 depicts in cross-sectional elevation view the reference electrode probe of the present invention.

These drawings will be described in detail below.

DETAILED DESCRIPTION OF THE INVENTION

While having utility in a broad variety of industrial monitoring functions, the electrode probe structure of the instant invention finds particular utility operating under the rigorous environment of the reactor core of a nuclear power facility. No elastomeric seals or polymeric components are present in it structure which incorporates a sealing architecture of the highest integrity. In the latter regard, a brazed and welded assembly consisting only of ceramic and metal parts forms the structure of the device. The electrode finds employment as a standard or reference electrode. For a detailed discussion in connection with the above, reference is made to *Physical Chemistry* by G. W. Castellan, Chapter 17, "Equilibria in Electrochemical Cells", pp 344–382, Addison-Wesley Publishing Co., Reading Mass. (1964).

Referring to the drawing, the structure of the probe of the present invention is seen to be comprised of four principal components: electrode 10, annular support sleeve 12, signal transfer assembly 14, and first electrical conductor 16. Referring initially to electrode 10, it will be observed that zirconia tube or crucible 18 has closed end 20 and open end 22. The zirconia crucible desirably is partially stabilized, e.g. with 8% by weight yttria. Closed end 20 of crucible 18 is packed with metal/metal oxide powder 24. A variety of metal/metal oxide couples are appropriate depending on the particular requirements of the reference electrode. The preferred couple is copper/copper oxide for forming a copper/copper oxide/zirconia electrode. Additional metal/metal oxides include, for example, tin/tin oxide, bismuth/bismuth oxide, iron/iron oxide, and the like. Metal/metal oxide powder 24 is retained with crucible 18 by mineral insulating packing 26. Appropriate packing includes, for example, mineral wool, glass fiber, various ceramic fibers or wool, and the like. Mineral insulating packing 26 not only maintains metal/metal oxide bed 24 within crucible 18, but also electrically isolates metal/metal oxide 24 from contact with other metal housing components of the probe structure. Additionally, after having packed crucible 18 with metal/metal oxide bed 24, packing 26, when inserted in opening 22, wipes the interior surface of crucible 18 of any metal/metal oxide powder adhering to the interior walls. Again, removing powder from the walls of crucible 18 about opening 22 insures electrical isolation of the metal/metal oxide powder from the metal housing components of the probe.

Supporting sleeve 12 is seen to include first annular metal sleeve 28 which has distal open end 30 and proximal open and 32. While sleeve 28 can be fabricated from a single metal, it also is possible to employ two abutting sleeves as depleted in the drawing. Specifically, it will be observed that first annular sleeve 28 is welded at juncture 34 to second annular metal sleeve 36 which second annular sleeve has proximal end 32. It will be observed that the distal end of sleeve 28 has land 38 upon which open end 22 of crucible 18 rests. Sleeve 28 desirably is manufactured from a material that exhibits a coefficient of thermal expansion that is compatible with the ceramic material forming crucible 18. Kovar comprises the preferred metal for use in forming annular metal sleeve 28. Kovar comprises a group of alloys, e.g. Fe 53.8%, Ni 29%, Co 17%, and Mn 0.2%, which exhibit a coefficient of thermal expansion compatible with that of the zirconia material used in forming crucible 18. Other materials may be used in forming annular metal sleeve 28, providing that the coefficient of thermal expansion between the material is carefully matched.

Since the joining of crucible 18 to sleeve 28 should provide a hermetic seal, appropriate dimensional tolerances are maintained so that a snug fit of proximal open end 22 of crucible 18 into distal open end 30 of sleeve 28 results. For providing the hermetic seal, the zirconia tube first is painted with tungsten paint followed by the conducting of a firing operation. The fired zirconia crucible then is nickel-plated and sintered. The interior surface of sleeve 28 about distal end 30 also is nickel-plated, fired, and these operations repeated. The surfaces to be joined now have a metal coating that is conducive to acceptance of the braze metal or alloy utilized in the joining operation. Preferably, a silver braze is used to join crucible 18 to sleeve 28.

As noted above, kovar sleeve 28 is joined to sleeve 36 at weld 34 which may be conducted utilizing tungsten inert gas (TIG) welding techniques. The material of construction for annular transition sleeve 36 preferably is stainless steel for providing corrosion resistance and minimizing costs associated to fabrication of the reference probe of the present invention.

Signal transfer assembly 14 is seen to be positioned within proximal opening 32 of sleeve 12. Positioning assembly 14 is seen to include stainless steel collar 40 that is welded to sleeve 36, such as by TIG welding, to provide a hermetic seal. Ceramic support 42, inwardly adjacent to collar 40, houses electrical connection from the outside to the interior of the electrode probe of the present invention. Specifically, insulated retainer 44 houses a nickel tube which is connected at its proximal end to coax cable 46 and to its distal end to first electrical conductor 16. Support assembly 14 is commercially available and marketed, for example, by Reutor-Stokes, a Division of General Electric Company, Twinsburg, Ohio. Should the yttria crucible fail, water containing radioactive material will not leak to the outside by virtue of the seal provided by the connection of collar 40 to sleeve 36.

The final component comprises first electrical conductor 16. The distal end of conductor 16 desirably is bent into a hook or ring-like configuration which is pushed against closed end 20 of crucible 18 (not shown in the drawing). The packing of metal/metal oxide 24 about conductor 16 provides good electrical contact therebetween. Electrical conductor 16 then passes through packing 26 and out of open end 22 of crucible 18 into the space provided within annular sleeve 12. While conductor 16 can be clad with ceramic insulation, preferably, annular ceramic sleeve 48 is nested within annular sleeve 12 and provides for electrical insulating of conductor 16 from the metallic housing of the probe. Annular electrical insulator 48 generally is manufactured from ceramic material, such as alumina. It will be observed that spring or coil section 50 is provided for conductor 16 for insuring that the electrical connector always is pushing against its contact ends. Additionally, the coil section protects against conductor breakage by allowing for expansion and contraction of conductor 16 during heating an cooling cycles. First electrical conductor 16 terminates at its proximal end by being welded to the nickel tube provided within positioning assembly 14.

It will be appreciated that the components described preferably are cylindrical in shape, though it will be appreciated that other shapes may be sued. For example, crucible 18, sleeves 28 and 36, and insulator 48 can be square, hexagonal, or of other geometric configuration.

With respect to performance specifications of the inventive reference electrode probe, the probe is designed to operate at temperatures ranging up to about 600° F. and pressures of up to about 2,000 psi. The novel reference electrode should exhibit a voltage that is within ±0.020 volts of the theoretical value for the metal/metal oxide/zirconia electrode sensor used in constructing the probe. The inventive reference electrode probe is capable of measuring ECPs to within ±0.010 volts in constant water chemistry.

Referring to FIG. 2, two sensing platinum electrode probes were subjected to laboratory testing utilizing the inventive reference probe fabricated to be a copper/copper oxide/$ZrO_2$ reference electrode probe. The aqueous medium for testing was provided by an autoclave within which temperature and water chemistry were controlled. The test was carried out at a water temperature of 274°C. and in conjunction with a sequence of aqueous conditions wherein certain dissolved gases were introduced. A first such dissolved gas was hydrogen, as labeled along the elapsed time portion of the figure as represented at 60, and represents hydrogen water chemistry (HWC). Thereafter, as labeled along the elapsed time portion of the figure as represented at 62, oxygen was injected into the aqueous medium, thus subjecting the probes to normal boiling water chemistry (NWC). This sequence was repeated by establishing hydrogen water chemistry again as represented at 64 followed by the establishment of normal water chemistry as represented at 66. As the potential of the inventive reference electrode probe can be calculated, its potential under the various water conditions can be subtracted from the voltage obtained, thus enabling a measurement of the ECP of the two different platinum electrode probes. The results of the two platinum electrode probes evaluated are represented at 68 and 70. It will be observed that a shift in the ECP results by virtue of the water chemistry involved. It is this shift that is monitored during use of the inventive reference electrode probe for determining the water chemistry of the aqueous medium being tested. The expected shift in ECP can be seen by reference to FIG. 2.

Since certain changes may be made in the above-described apparatus without departing from the scope of the invention, the description and accompanying drawings shall be interpreted as illustrative and not in a limiting sense in accordance with the precepts of the invention disclosed herein.

We claim:

1. A reference electrode probe for use in monitoring electrochemical potentials, which comprises;
   (a) a zirconia crucible having a closed end and an open end, the closed end containing metal/metal oxide powder and being retained therein by mineral insulating packing;
   (b) a first annular metal sleeve formed of a metal exhibiting a coefficient of thermal expansion compatible with said zirconia crucible, and having a distal open end in sealing engagement with said zirconia crucible open end, and a proximal open end;
   (c) an insulated first electrical conductor having a distal end in electrical connection with said metal/metal oxide powder and extending through said mineral insulation packing and into said first annular sleeve, and having a proximal end terminating near the proximal end of said first annular sleeve; and
   (d) a signal transfer assembly sealingly associated with said proximal end of said first annular sleeve and through which is second electrical conductor passes to its electrical connection with said first electrical conductor.

2. The reference electrode probe of claim 1 wherein said first electrical conductor is insulated by an annular electrical insulator housed within said first annular metal sleeve.

3. The reference electrode probe of claim 2 wherein said annular electrical insulator is formed of alumina.

4. The reference electrode probe of claim 1 wherein said signal transfer assembly includes an annular metal sleeve through which said second electrical conductor passes.

5. The reference electrode probe of claim 1 wherein a second annular metal transition sleeve is interposed between said first annular metal sleeve and said signal transfer assembly, said second metal transistion sleeve being formed of a different material than said first annular metal sleeve.

6. The reference electrode probe of claim 5 wherein said second metal transition sleeve is formed of stainless steel.

7. The reference electrode probe of claim 1 wherein said first electrical conductor is a wire formed of a material selected from the group consisting of platinum, a kovar, copper, and stainless steel.

8. The reference electrode probe of claim 1 wherein said metal/meal oxide powder is selected from the group consisting of copper/copper oxide, tin/tin oxide, bismuth/bismuth oxide, and iron/iron oxide.

9. The reference electrode probe of claim 8 wherein said metal/metal oxide powder comprises copper/copper oxide powder.

10. The reference electrode probe of claim 1 wherein said first annular metal sleeve is formed of kovar.

11. A reference electrode probe for use in monitoring electrochemical potentials which comprises;
    (a) a zirconia crucible having a closed end and an open end, the closed end containing metal/metal oxide powder and being retained therein by mineral insulation packing;
    (b) a kovar annular cylindrical sleeve having a distal open end brazed with said zirconia crucible open end, and a proximal open end;
    (c) an annular ceramic electrical insulating cylinder housed within said kovar annular cylinder substantially its entire extent;
    (d) a first electrical conductor wire having a distal end in electrical connection with said metal/metal oxide powder and extending through said mineral insulation packing and into said annular ceramic insulating cylinder, and having a proximal end terminating near the proximal end of said kovar cylindrical sleeve; and (e) a signal transfer assembly including a metal collar welded to the proximal end of said kovar annular sleeve and through which a second electrical conductor wire passes to its electrical connection with said first electrical conductor wire.

12. The reference electrode probe of claim 11 wherein a stainless steel annular cylindrical transition sleeve is welded to said kovar annular cylinder, said transition sleeve having a outlet to which said metal collar is welded.

13. The reference electrode probe of claim 12 wherein said metal/metal oxide powder is selected from the group consisting of copper/copper oxide, tin/tin oxide, bismuth/bismuth oxide, and iron/iron oxide.

14. The reference electrode probe of claim 13 wherein said first conductor wire is formed of a material selected from the group consisting of platinum, kovar, copper, and stainless steel.

15. The reference electrode probe of claim 14 wherein said zirconia crucible is metalized about its open end for being brazed to said kovar annular sleeve.

16. The reference electrode probe of claim 15 wherein said kovar annular sleeve about its distal end is metalized for brazing to said zirconia crucible open end.

* * * * *